(12) United States Patent
Nava

(10) Patent No.: US 7,018,367 B2
(45) Date of Patent: Mar. 28, 2006

(54) URINE COLLECTION ASSEMBLY FOR MALES

(76) Inventor: Jorge L. Nava, 412 E. Polk Ave., Pharr, TX (US) 78577

( * ) Notice: Subject to any disclaimer, the term of this patent is extended or adjusted under 35 U.S.C. 154(b) by 421 days.

(21) Appl. No.: 10/436,733

(22) Filed: May 14, 2003

(65) Prior Publication Data

US 2004/0230134 A1    Nov. 18, 2004

(51) Int. Cl.
*A61F 5/44* (2006.01)

(52) U.S. Cl. .................. 604/349; 604/351; 604/144.3; 600/573; 4/144.3

(58) Field of Classification Search ................ 600/573, 600/580; 604/327, 346, 347, 349, 351; 4/144.1, 4/144.4, 144.3
See application file for complete search history.

(56) References Cited

U.S. PATENT DOCUMENTS

| | | | | |
|---|---|---|---|---|
| 3,604,424 A | * | 9/1971 | Windom | .................. 604/350 |
| 3,835,857 A | * | 9/1974 | Rogers et al. | ............... 604/349 |
| 4,957,487 A | * | 9/1990 | Gerow | ........................ 604/133 |
| 5,318,550 A | * | 6/1994 | Cermak et al. | ............. 604/349 |

* cited by examiner

*Primary Examiner*—Max F. Hindenburg
*Assistant Examiner*—Jonathan Foreman

(57) ABSTRACT

A urine collection assembly for males for allowing a male passenger in a vehicle to relieve oneself discreetly and sanitarily without having to stop the vehicle. The urine collection assembly for males includes a container assembly including a container having top and bottom walls and also having a drainage opening being disposed through the bottom wall, and also including a cap being removably disposed over the drainage opening; and also includes a fastening assembly for fastening the container to a user's body; and further includes a conduit assembly including a first hose being connected to the container; and also includes a male organ attachment assembly including a flexible sleeve being removably disposed about a male urinary organ, and also including a funnel being connected to the flexible sleeve and to the hose.

2 Claims, 3 Drawing Sheets

URINE COLLECTION ASSEMBLY FOR MALES

BACKGROUND OF THE INVENTION

1. Field of the Invention

The present invention relates to male urine collection systems and more particularly pertains to a new urine collection assembly for males for allowing a male passenger in a vehicle to relieve oneself discreetly and sanitarily without having to stop the vehicle.

2. Description of the Prior Art

The use of male urine collection systems is known in the prior art. More specifically, male urine collection systems heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,713,067; U.S. Pat. No. 4,073,295; U.S. Pat. No. 5,312,383; U.S. Pat. No. 5,318,550; U.S. Pat. No. 5,439,456; U.S. Pat. No. 6,007,521; and U.S. Pat. No. Des. 357,979.

While these devices fulfill their respective, particular objectives and requirements, the aforementioned patents do not disclose a new urine collection assembly for males. The prior art includes funnels and hoses and collection devices for collecting urine.

SUMMARY OF THE INVENTION

The general purpose of the present invention, which will be described subsequently in greater detail, is to provide a new urine collection assembly for males which has many of the advantages of the male urine collection systems mentioned heretofore and many novel features that result in a new urine collection assembly for males which is not anticipated, rendered obvious, suggested, or even implied by any of the prior art male urine collection systems, either alone or in any combination thereof. The present invention includes a container assembly including a container having top and bottom walls and also having a drainage opening being disposed through the bottom wall, and also including a cap being removably disposed over the drainage opening; and also includes a fastening assembly for fastening the container to a user's body; and further includes a conduit assembly including a hose being connected to the container; and also includes a male organ attachment assembly including a flexible sleeve being removably disposed about a male urinary organ, and also including a funnel being connected to the flexible sleeve and to the hose. None of the prior art includes the combination of the elements of the present invention.

There has thus been outlined, rather broadly, the more important features of the urine collection assembly for males in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is an object of the present invention to provide a new urine collection assembly for males which has many of the advantages of the male urine collection systems mentioned heretofore and many novel features that result in a new urine collection assembly for males which is not anticipated, rendered obvious, suggested, or even implied by any of the prior art male urine collection systems, either alone or in any combination thereof.

Still another object of the present invention is to provide a new urine collection assembly for males for allowing a male passenger in a vehicle to relieve oneself discreetly and sanitarily without having to stop the vehicle.

Still yet another object of the present invention is to provide a new urine collection assembly for males that is easy and convenient to use.

Even still another object of the present invention is to provide a new urine collection assembly for males that prevents urinary and bladder problems by the user having to prevent going to the bathroom until a suitable location is found.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
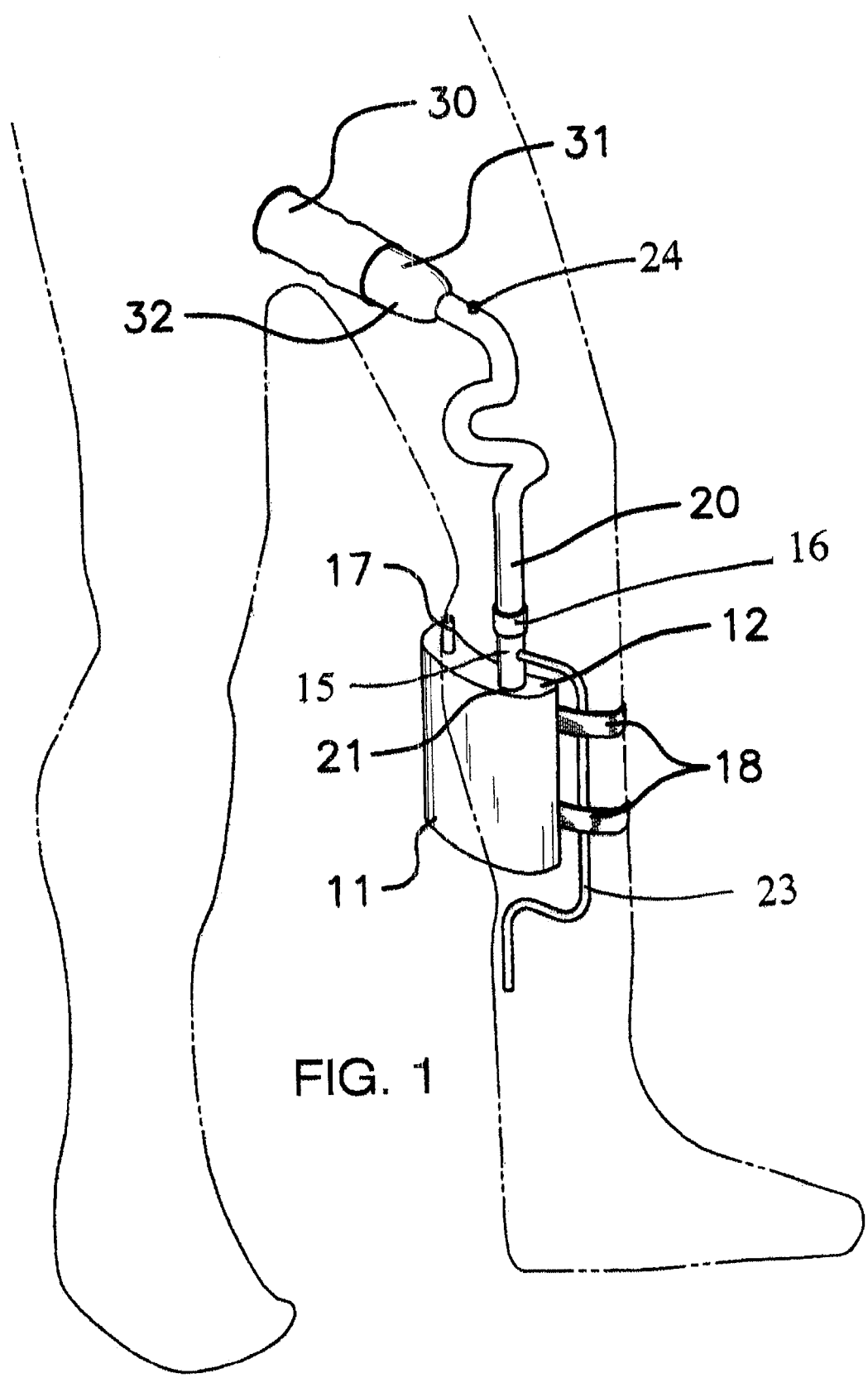
FIG. 1 is a perspective view of a new urine collection assembly for males according to the present invention.
Figure 2:
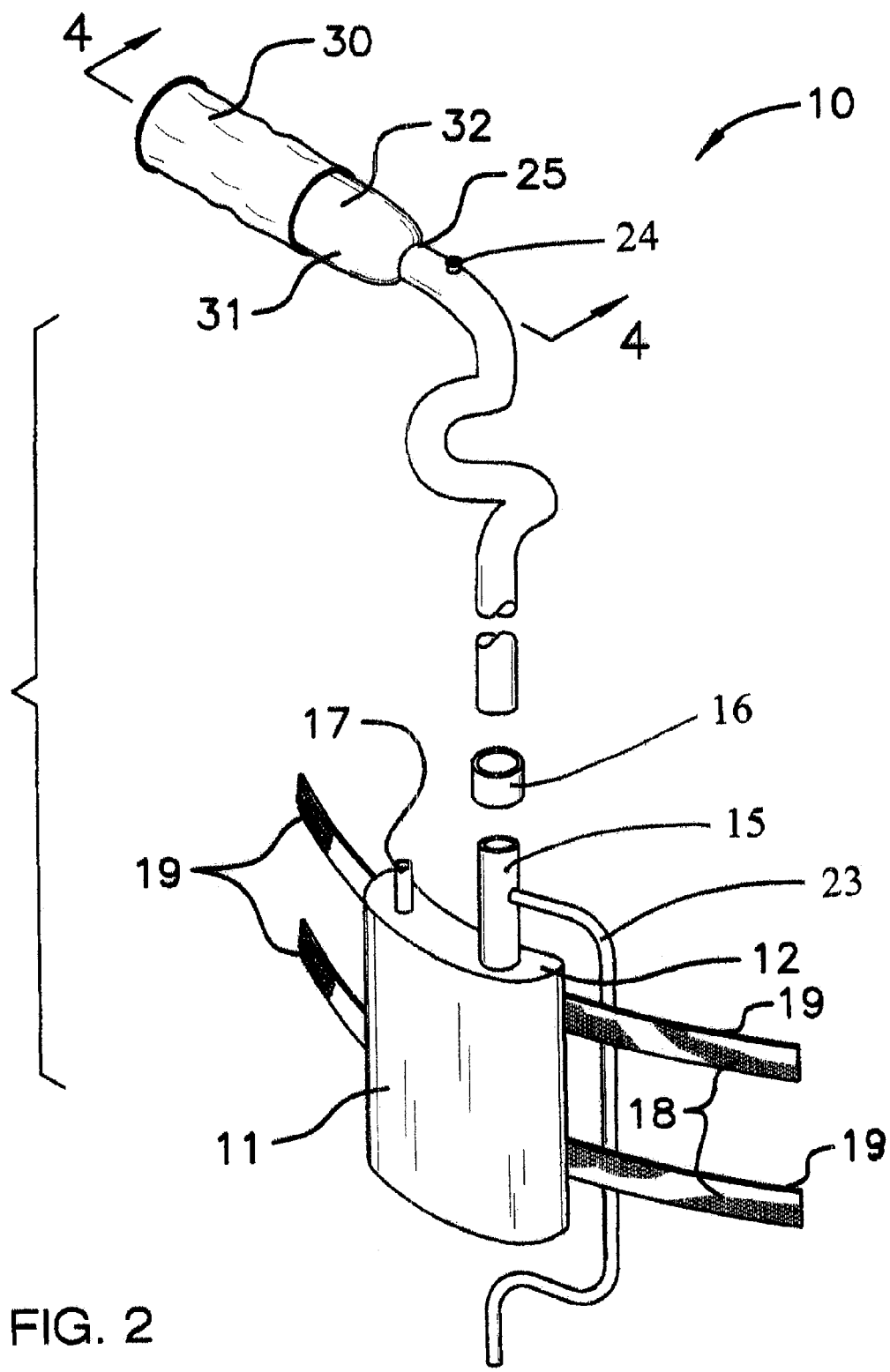
FIG. 2 is an exploded perspective view of the present invention.
Figure 3:
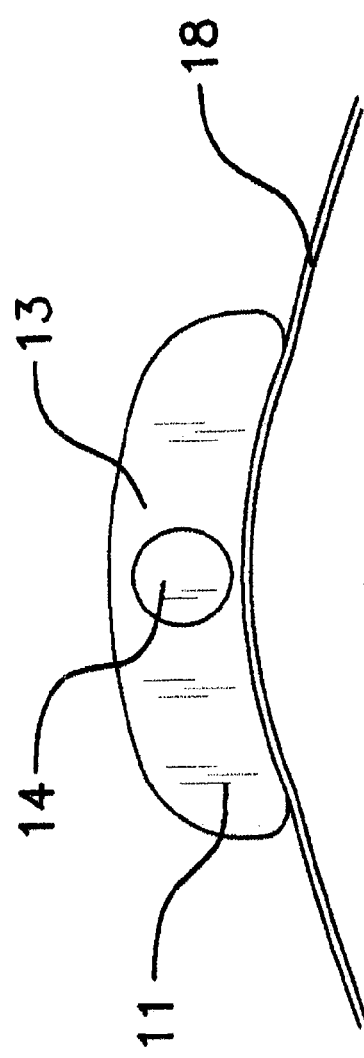
FIG. 3 is a bottom plan view of the container of the present invention.
Figure 4:
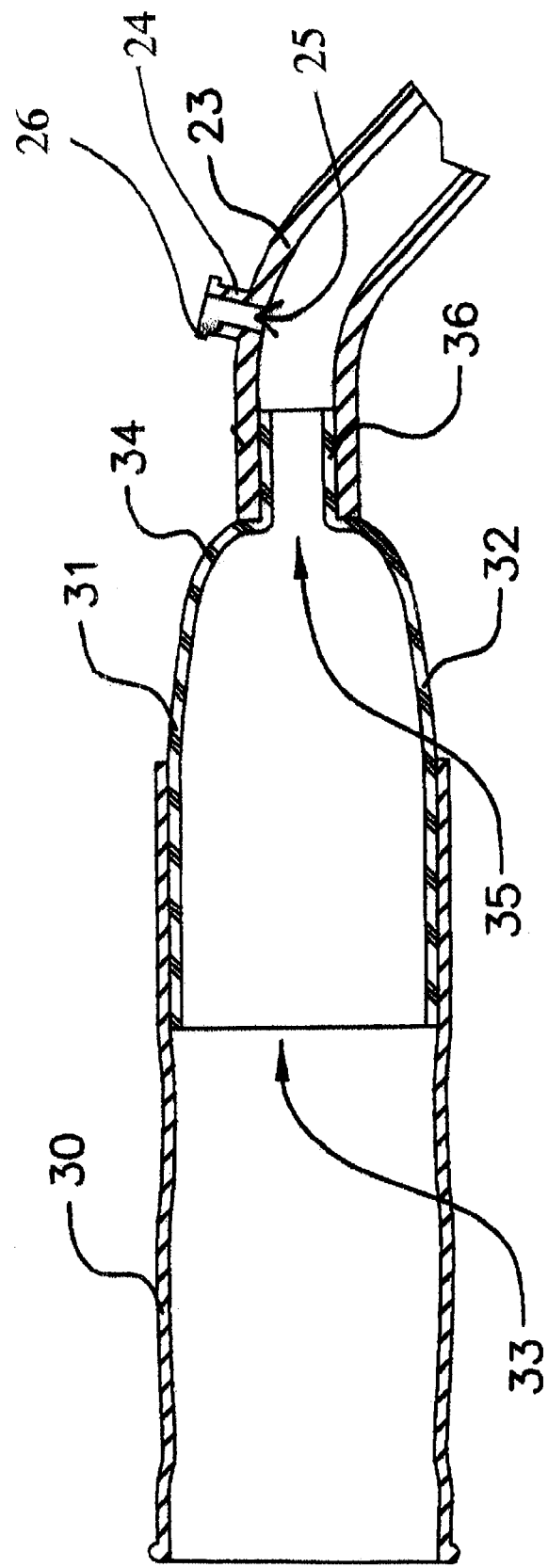
FIG. 4 is a cross-sectional view of the sleeve and funnel of the present invention.

With reference now to the drawings, and in particular to FIGS. 1 through 4 thereof, a new urine collection assembly for males embodying the principles and concepts of the present invention and generally designated by the reference numeral 10 will be described.

As best illustrated in FIGS. 1 through 4, the urine collection assembly for males 10 generally comprises a container assembly including a container 11 having top and bottom walls 12,13 and also having a drainage opening being disposed through the bottom wall 13, and also including a cap 14 being removably and securely disposed over the drainage opening. The container 11 also includes a tubular air outlet member 17 being securely disposed in the top wall 12 of the container 11, and further includes a tubular fluid-receiving member 15 being securely disposed in the top wall 12 of the container 11, and also includes a hose connector member 16 being conventionally attached at a top end of the tubular fluid receiving member 15, and further includes a tubular air ventilation member 23 being conventionally attached to and disposed through a wall of the tubular fluid-receiving member 15 for ventilating the tubular fluid-receiving member 15.

A fastening assembly for fastening the container 11 to a user's body includes straps 18 being securely attached by any suitable means to a side wall of the container 11 and having first and second end portions, and also includes strips of hook and loop fasteners 19 being securely attached and sewn at the first and second end portions with the straps 18 being adapted to fasten about a user's leg for supporting the container 11 to the user's leg.

A conduit assembly includes a hose 20 being removably and engageably and conventionally connected to the hose connector member 16. The hose 20 has a first end 21 which is fastenably and conventionally received in the hose connector member 16 and also has a second end 22. The conduit assembly further includes an air ventilating boss 24 being conventionally disposed in a wall of the hose 20 near the second end 22 thereof. The air ventilating boss 24 has a bore 25 being disposed therethrough and into the hose 20, and also has an annular flange 26 being conventionally disposed about an outer rim thereof for connecting to an air hose.

A male organ attachment assembly includes a flexible sleeve 30 being adapted to be removably disposed about a male urinary organ, and also includes a funnel 31 being securely connected to the flexible sleeve 30 and to the hose 20. The funnel 31 includes a conical-shaped portion 32 having an open end 33 and a closed end 34 with a hole 35 being disposed through the closed end 34, and also includes a tubular stem portion 36 being integrally disposed about the hole 35 and extending outwardly from the conical-shaped portion 32 and being removably engaged in the second end 22 of the hose 20. The flexible sleeve 30 has an end portion which is removably and engageably disposed about the open end 33 of the funnel 31.

In use, the user slips the flexible sleeve about one's male urinary organ with the conduit assembly being connected to the funnel 31 and to the container 11, and the user simply urinates in the flexible sleeve 30 with the urine passing through the funnel 31 and through the hose 20 and into the container 11; whereupon, the user can empty the contents by removing the cap 14 from the container 11. The tubular air ventilating member 16 and the tubular air outlet member 17 equalizes the air pressure in the conduit assembly and the container 11.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the urine collection assembly for males. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A urine collection assembly for males comprising:
    a container assembly including a container having top and bottom walls and also having a drainage opening being disposed through said bottom wall, and also including a cap being removably disposed over said drainage opening, said container also including a tubular air outlet member being disposed in said top wall of said container, and further including a tubular fluid-receiving member being disposed in said top wall of said container, and also including a hose connector member being attached at a top end of said tubular fluid receiving member, and further including a tubular air ventilation member being attached to and disposed through a wall of said tubular fluid-receiving member for ventilating said tubular fluid-receiving member;
    a fastening assembly for fastening said container to a user's body, said fastening assembly including straps being securely attached to a side wall of said container and having first and second end portions, and also including strips of hook and loop fasteners being attached at said first and second end portions, said straps being adapted to fasten about a user's leg for supporting said container to the user's leg;
    a conduit assembly including a hose being connected to said container, said hose having a first end which is removably and engageably received in said hose connector member, and also having a second end, said conduit assembly further including an air ventilating boss being conventionally disposed in a wall of said hose near said second end thereof, said air ventilating boss having a bore being disposed therethrough and into said hose, and also having an annular flange being conventionally disposed about an outer rim thereof for connecting to an air hose; and
    a male organ attachment assembly including a flexible sleeve adapted to being removably disposed about a male urinary organ, and also including a funnel being connected to said flexible sleeve and to said hose.

2. The urine collection assembly for males as described in claim 1, wherein said funnel includes a conical-shaped portion having an open end and a closed end with a hole being disposed through said closed end, and also includes a tubular stem portion being disposed about said hole and extending outwardly from said conical-shaped portion and being removably engaged in said second end of said hose, said flexible sleeve having an end portion which is removably and engageably disposed about said open end of said funnel.

\* \* \* \* \*